(12) United States Patent
Durlach

(10) Patent No.: US 9,029,419 B2
(45) Date of Patent: May 12, 2015

(54) USE OF ZINC N-ACETYLTAURINATE

(75) Inventor: Jean Durlach, Neuilly sur Seine (FR)

(73) Assignee: TRI-INOV, Neuilly sur Seine (FR)

( * ) Notice: Subject to any disclaimer, the term of this patent is extended or adjusted under 35 U.S.C. 154(b) by 0 days.

(21) Appl. No.: 12/918,990

(22) PCT Filed: Feb. 25, 2009

(86) PCT No.: PCT/FR2009/050297
§ 371 (c)(1),
(2), (4) Date: Aug. 27, 2010

(87) PCT Pub. No.: WO2009/112758
PCT Pub. Date: Sep. 17, 2009

(65) Prior Publication Data
US 2011/0003891 A1    Jan. 6, 2011

(30) Foreign Application Priority Data

Feb. 26, 2008  (FR) .................................. 08 51233

(51) Int. Cl.
*A61K 31/315*    (2006.01)
*A61K 31/185*    (2006.01)

(52) U.S. Cl.
CPC .................................. *A61K 31/185* (2013.01)

(58) Field of Classification Search
CPC .................................................. A61K 31/185
USPC ......................................................... 514/578
See application file for complete search history.

(56) References Cited

U.S. PATENT DOCUMENTS

| 4,199,601 | A |   | 4/1980 | Durlach |         |
|-----------|---|---|--------|---------|---------|
| 4,271,189 | A | * | 6/1981 | Durlach | 514/578 |
| 6,103,756 | A |   | 8/2000 | Gorsek  |         |
| 6,573,299 | B1| * | 6/2003 | Petrus  | 514/558 |
| 7,056,942 | B2| * | 6/2006 | Hildesheim et al. | 514/411 |
| 2005/0249821 | A1 |  | 11/2005 | Paul |       |

FOREIGN PATENT DOCUMENTS

| FR | 2384751 |      | 10/1978 |
|----|---------|------|---------|
| WO | WO 2005/027950 | A1 | 3/2005 |

OTHER PUBLICATIONS

Pasantes-Morales et al.; Protective Effect of Taurine and Zinc on Peroxidation-Induced Damage in Photoreceptor Outer Segments; Journal of Neuroscience Research 11:303-311 (1984).*
Prevent definition; Merrian-Webster dictionary; accessed online Jul. 9, 2012.*
Prophylaxis definition; Merrian-Webster dictionary; accessed online Jul. 9, 2012.*
Changemi Francis E "TOZAL Study: an open case control study of an oral antioxidant and omega-3 supplement for dry AMD" BMC Ophtahalmology 2007, vol. 7, No. 3, 2007, XP002496218, ISSN: 1471-2415.
Harraki B et al."Effect of taurine, L-glutamine and L-histidine addition in an amino acid glucose solution on the cellular bioavailability of zinc." Biometals: An-International Journal on the Role of Metal Ions in Biology, Biohchemistry, and Medicine Jul. 1994, vol. 7, No. 3 Jul. 1994, pp. 237-243, XP002496219, ISSN: 0966-0844.
Gottschall-Pass K T et al. "Oscillatory potentials and light microscopic changes demonstrate an interaction between zinc and taurine in the developing rat retina", The Journal of Nutrition Jun. 1997, vol. 127, No. 6, Jun. 1997, pp. 1206-1213, XP002496220, ISSN: 0022-3166.
Grahn Bruce H et al. "Zinc and the eye" Journal of the American College of Nutrition, American College of Nutrion, Wilmington, NC, US, vol. 20, No. 2 with Supplement, Apr. 1, 2001, pp. 106-118, XP002334806, ISSN: 0731-5724.
M. Teraoka "Uber die Methylierung und Acylierung des Taurins (On the Methylation and Acylation of Taurine)", Hoppe-Seyler Zeitschrift für Physiologische Chemie, 145, 242 (1925) with English translation.
Francis E Cangemi "TOZAL Study: an open case control study of an oral antioxidant and omega-3 supplement for dry AMD" BMC Ophtahalmology 2007, vol. 7, No. 3, 2007, XP002496218, ISSN: 1471-2415.
Bartlett et al., "Age-related macular degeneration and nutritional supplementation: a review of randomized controlled trials", Opthal, Physiol. Opthal, Physiol. Opt. 2003, 23: 383-399.
Bartlett et al., "Risk Factors Associated with Age-Related Macular Disease", Optometry in practice, vol. 5 (2004) 15-32).
Li X et al. "Diabetes and Methallothionein", Mini-Reviews in Medical Chemistry 2007;7:761-768.
Dunn K.C. et al., "ARPE-19, A Human Retinal Pigment Epithelial Cell Line with Differentiated Properties". *Exp Eye Res*. 1996;62: 155-169.
Alizadeh M et al., "Downregulation of Differentiation specific Gene Expression by Oxidative Stress in ARPE-19 cells". Invest Opthalmol Vis Sci 2001; 42: No. 11: 2706-2707.
Hui Cai et al. "Gene expression profile of cultured adult compared to immortalized human retinal pigment epithelium" Molecular Vision 2006, 12: 1-14.
Ishida BY et al. "High density lipoprotein mediated lipid efflux from retinal pigment epithelial cells in culture", Br J Ophtalmol 2006; 90: 616-620.

* cited by examiner

*Primary Examiner* — Jim Ketter
*Assistant Examiner* — Antonio Galisteo Gonzalez
(74) *Attorney, Agent, or Firm* — Hamre, Schumann, Mueller & Larson, P.C.

(57) ABSTRACT

The subject matter of the present invention is Zn N-acetyltaurinate of formula: $[CH_3-CO-NH-CH_2-CH_2-SO_3]_2^- Zn^{2+}$ for preventing and/or treating diseases with lipofuscin accumulation due in particular to aging or to oxidative stress, and for preparing a medicament that is of use in treating these diseases.

Use: treatment of diseases related to aging or to oxidative stress, in particular age-related macular degeneration and diabetic retinopathy.

7 Claims, 4 Drawing Sheets

* p<0.05 relative to the carrier  n=6)

* p<0.05 relative to $H_2O_2$ (n=4)

* $p<0.05$ relative to the carrier
* $p<0.05$ relative to $H_2O_2$ alone (n=4)

* p<0.05 relative to $H_2O_2$ (n=4)

* p<0.05 relative to the carrier (n=4)

USE OF ZINC N-ACETYLTAURINATE

BACKGROUND OF THE INVENTION

The present invention relates to a novel use of zinc N-acetyltaurinate.

Zinc N-acetyltaurinate belongs to the family of taurine derivatives having improved neuromuscular activity, which are described in patent FR 2 384 751. It has now been found, surprisingly, that zinc N-acetyltaurinate (ATA-Zn) can be used for preventing and/or treating diseases with lipofuscin accumulation.

Lipofuscin accumulation can be due in particular to aging or to oxidative stress.

Aging is constituted of a collection of functional modifications which gradually decrease the ability of an individual to maintain his or her physiological equilibrium. One of the manifestations of aging is the accumulation, in the tissues, of lipofuscin, which is an autofluorescent, nondegradable substance; it constitutes the major mark of aging.

Oxidative stress (or oxidizing stress) is an attack on the cells and tissues resulting from a dysregulation of the oxidation reactions in the cells, which leads to the formation of toxic substances, such as free radicals (or reactive oxygen species (ROS)). Oxidative stress can affect all tissues and metabolisms, and participate in aging and in a large number of pathological conditions, such as cardiovascular diseases (atherothrombosis), cancers, inflammatory diseases, metabolic diseases (diabetes mellitus, obesity) and degenerative diseases, such as Alzheimer's disease, Parkinson's disease, cataracts or age-related macular degeneration. Age-related macular degeneration (ARMD) is the most common cause of partial-sightedness in industrialized countries among adults over the age of 55. It manifests itself through a thickening of the macular zone of the retina or atrophy of this zone, and sometimes through bleeding (Opthal, Physiol. Opt. 2003, 23:383-399 and Optometry in practice, vol. 5 (2004) 15-32).

Zinc is very concentrated in the ocular tissues, in particular in the retina and in the pigmentary epithelium. It acts as a cofactor for antioxidant enzymes (retinal catalase and dehydrogenase).

Antioxidants, such as vitamins C and E, carotenoids and zinc can limit the risks of progression of age-related macular degeneration.

In particular, it has been demonstrated that zinc plays an important role in maintaining normal ocular functions and that the use of zinc as a food supplement can reduce the aging process in mice (Journal of the American college of nutrition, 2001, vol. 20, No. 2, 106-118). It is also known that zinc appears to have a fundamental role in the prevention of diabetes mellitus and complications thereof. (Li X et al. Diabetes and methallothionein. *Mini-Reviews in Medical Chemistry* 2007; 7:761-768).

However, the use of zinc as a food supplement should be considered with care since an excess of zinc can lead to toxic effects.

In addition, studies have shown that taurine interacts closely with zinc in the development of the retina in rats (J. Nutr. 1997, June; 127(6):1206-13) and that taurine, as a food supplement, increases zinc absorption via the fibroblasts (Biometals, 1994, 7, 237-243).

SUMMARY OF THE INVENTION

It has now been found, surprisingly, that zinc N-acetyltaurinate can prevent and/or treat diseases with lipofuscin accumulation which result, in particular, from aging or from oxidative stress, in particular diseases of the retina and especially age-related macular degeneration and diabetic retinopathy.

Thus, the present invention relates to zinc N-acetyltaurinate of formula:

$[CH_3-CO-NH-CH_2-CH_2-SO_3]_2{}^-Zn^{2+}$ for preventing and/or treating diseases with lipofuscin accumulation resulting, in particular, from aging or oxidative stress, in particular diseases of the retina, especially for preventing and/or delaying age-related macular degeneration and diabetic retinopathy.

The invention also relates to the use of zinc N-acetyltaurinate of formula:

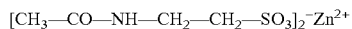

$[CH_3-CO-NH-CH_2-CH_2-SO_3]_2{}^-Zn^{2+}$ for the manufacture of a medicament for the prevention and/or treatment of lipofuscin accumulation-related diseases resulting, in particular, from aging or to oxidative stress, in particular diseases of the retina, especially in preventing and/or delaying age-related macular degeneration and diabetic retinopathy.

DETAILED DESCRIPTION

Figure 1:
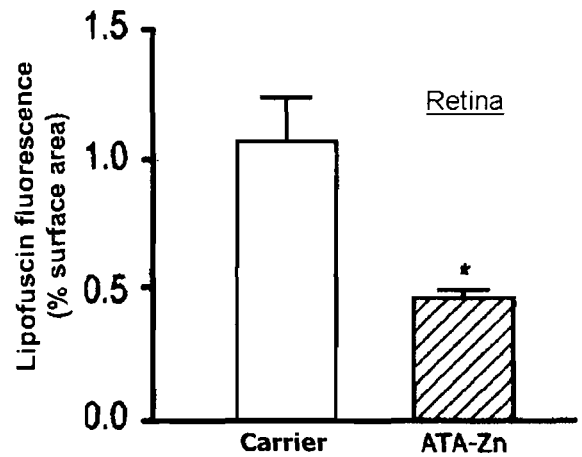
FIGS. 1-3 are graphs showing lipofucsin fluorescence in the retina, prostate and hippocampus respectively after administration of carrier or ATA-Zn.

The zinc N-acetyltaurinate is prepared by reacting acetic anhydride with taurine in the presence of zinc acetate according to a process similar to that described for the preparation of sodium N-acetyltaurinate by M. Terakoa (Hoppe-Seyler Zeitschrift für Physiologische Chemie, 145, 242 (1925)).

Preferably, zinc N-acetyltaurinate dihydrate is used.

For the administration to patients suffering from diseases related to lipofuscin accumulation relating from aging or oxidative stress, such as in particular diseases of the retina, in particular age-related macular degeneration and diabetic retinopathy, the zinc N-acetyltaurinate is mixed, as active ingredient, with a pharmaceutically acceptable excipient commonly used for preparing pharmaceutical compositions that can be administered orally, parenterally or locally.

Advantageously, the zinc N-acetyltaurinate can be provided in forms that can be administered:
  orally, such as tablets, sugar-coated tablets, capsules, gel capsules, sachets, solutions, containing the active ingredient at the unit dose of from 0.06 to 1 g and, for the solutions, from 0.6 to 5 g per 10 ml;
  parenterally, such as injectable solutions packaged in vials, containing from 0.1 to 2 g of active ingredient per vial;
  locally, such as lotions, creams, ointments, solutes, eye-drop solutions, etc.

The dose to be administered daily is generally from 0.06 to 10 g, and preferably from 1 to 2 g.

The activity of ATA-Zn on aging was measured by determining the amount of lipofuscin in certain tissues in aged rats (retina, prostate and hippocampus).

The antioxidant activity of zinc N-acetyltaurinate was demonstrated using the ARPE-19 retinal pigmented epithelial cell line, which constitutes a tool commonly used to study the physiology and pathology of the retina. This cell line has been described by:

a) Dunn K C et al., "a human retinal pigment epithelial cell line with differentiated properties". *Exp Eye Res.* 1996; 62:155-169;

b) Alizadeh M et al., "Downregulation of differentiation specific gene expression by oxidative stress in ARPE-19 cells". *Invest Opthalmol Vis Sci* 2001; 42:2706-13 c) Hui Cai et al. "Gene expression profile of cultured adult compared to immortalized human retinal pigment epithelium" *Molecular Vision* 2006, 12: 1-14.

d) Ishida B Y et al. High density lipoprotein mediated lipid efflux from retinal pigment epithelial cells in culture. *Br J Ophtalmol* 2006; 90:616-620.

The tests carried out, reported hereinafter, show that only zinc N-acetyltaurinate has an effect on the production of adenosine triphosphate (ATP) by the ARPE-19 cells treated with ATA-Zn and then exposed to an aqueous hydrogen peroxide solution ($H_2O_2$).

On the other hand, zinc alone or taurine alone has no effect.

Other tests have shown that the effect of zinc N-acetyltaurinate on ATP production by ARPE-19 cells is virtually identical to or even greater than the effect obtained with the comparative antioxidants, such as docosahexaenoic acid (DHA), lutein and zeaxanthin. Lutein and zeaxanthin are natural pigments of the carotenoid family which are concentrated in the macula and protect it against damages caused by oxidation or light. Lutein and zeaxanthin are natural food supplements used in the treatment of age-related macular degeneration.

The invention will now be described in more detail by means of the following preparation and assays.

Preparation 20.25 g of taurine and 17.5 g of dry pure zinc acetate were mixed together and 50 g of pure water was added.

The resulting suspension was heated to a temperature of between 65 and 75° C. and 45 g of acetic anhydride was added to this suspension and the mixture was then heated to 100-105° C. 100 ml of anhydrous ethanol was then added to the resulting reaction mixture at a temperature of between 70 and 75° C.

30±3 g of the expected product was finally obtained in the form of a white powder which is soluble in water and poorly soluble in ethanol (yield by weight: 36.25%).

Analysis (in Percentages)

| Analysis | Calculated | Found |
|----------|------------|-------|
| C | 24.16 | 22.75 |
| H | 4.05 | 4.60 |
| N | 7.04 | 5.73 |
| Zn* | 16.4 | 16.7 |

*assaying of Zn with EDTA

Pharmacological Assays

I) In Vivo Assay
a) Effect of Ata-Zn on the Intracellular Accumulation of Lipofuscin in the Retina, the Prostate and the Hippocampus of Aged Rats Male Sprague-Dawley albino rats, aged 16 months, were placed in standard plastic cages, in groups of 5, with water and food ad libitum. The living conditions of the animals were the following: day:night light cycle, 12:12 h, constant temperature of 22±2° C. and relative humidity of 60%.

For the chronic treatment, ATA-Zn was administered to the rats, per os, once a day, for 4 weeks, at the dose of 40 mg/kg (n=6). The control animals received only water (carrier) for the same period of time (n=6). 24 hours after the end of the treatment, the rats were anesthetized with equithesin (2.5 mg/kg, i.p.) and perfused transcardially with 1% paraformaldehyde and 1.25% glutaraldehyde in a 0.1% sodium cacodylate buffer (pH 7.4) obtained from arsenous anhydride and potassium acetate.

The samples of the tissues taken (retina, prostate and hippocampus) were then cut into small pieces (1 $mm^3$) on a cryostat and added to a mixture of formaldehyde and glutaraldehyde in a cacodylate buffer for 2 hours. The samples were then mixed with osmium tetroxide, dehydrated in increasing concentrations of acetone and toluene and, finally, embedded into blocks of resin (EPON resin). The pieces of tissues thus processed were examined under an Olympus BX-60 fluorescence microscope. The retina, the prostate and the hippocampus showed a clear and significant accumulation of lipofuscin.

Figure 2:
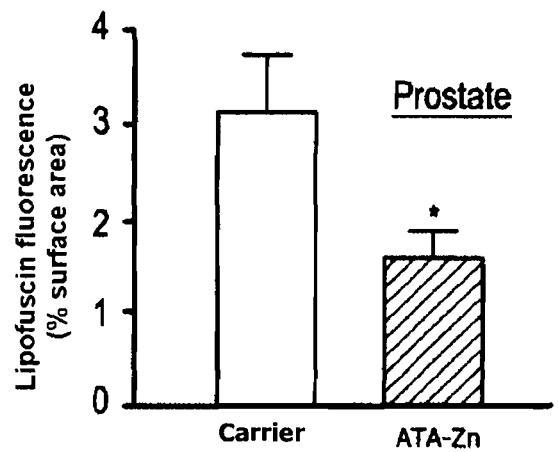
Figure 3:
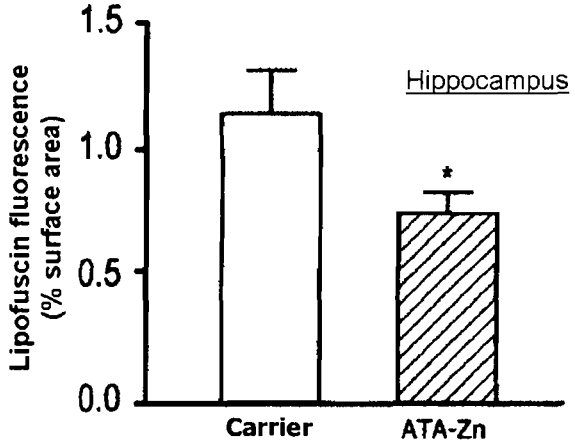

The fluorescence in all the tissues was quantified using an image analysis system (KS 300; Karl Zeiss). The analysis was carried out by measuring the percentage surface area hidden by the presence of fluorescence and compared with a standard zone of 2000 $\mu m^2$ (lipofuscin fluorescence expressed as % surface area relative to the standard zone) using an ×40 objective magnification and a Zeiss Sound Vision digital microscope video camera (total enlargement on the computer screen ×7500). The values measured in the areas with no fluorescence in the pieces of tissues were subtracted, as background noise, from the resulting binary image. The analysis was carried out by taking five different pieces per type of tissue (retina, prostate and hippocampus) per animal and by randomly selecting three different fields for each piece. The results, expressed as mean±standard deviation and analyzed using the t-test, are reported on FIGS. 1, 2 and 3, which represent histograms showing the fluorescence of the lipofuscin (% surface area) in the retina (FIG. 1), prostate (FIG. 2) and hippocampus (FIG. 3) tissues after administration of the carrier or the ATA-Zn.

The chronic administration of ATA-Zn at the dose of 40 mg/kg per as produced a significant reduction in the percentage surface area occupied by the lipofuscin fluorescence (positive) in the retina, the prostate and the hippocampus, of the aged rats, compared with the control animals.

This assay shows that ATA-Zn can inhibit lipofuscin accumulation resulting from aging in retina, hippocampus and prostate tissues.

II) In Vitro Assays
a) Materials and Methods

In the assays hereinafter described, the ARPE-19 human retinal pigmented epithelial cell line was used.

In order to assess the protective role of ATA-Zn with respect to an oxidative stress of the retinal epithelium, the following experimental model was used.

ARPE-19 cells grown in an appropriate medium [mixture of DMEM [Dulbecco's modified Eagle's medium) and Ham's F12 medium] containing 10% of heat-inactivated fetal calf serum; 2 mM glutamine; 0.1 mM of minimum essential medium; a solution of non-essential amino acids and gentamicin sulfate, in 96-well microplates, were exposed to various concentrations of an aqueous hydrogen peroxide solution ($H_2O_2$) being toxic for these cells. The cellular levels of ATP were measured using the commercially available assay which measures ATP production, "ATPLite-M", manufactured by Perkin Elmer, using a multiplate reader from Perkin Elmer Life Sciences, Boston, Mass. This assay is based on the principle that ATP production is dependent on cell viability and that a decrease or increase in ATP reflects a corresponding alteration in cell viability.

The protective effect of ATA-Zn was assayed by treating the ARPE-19 cells with ATA-Zn and subsequently exposing them to the aqueous hydrogen peroxide solution. Various exposure times and various doses were used. Comparative assays were also carried out. The results of these assays are reported in FIGS. 5 to 9, which are graphs showing the ATP production, expressed as a percentage relative to the ATP production by control cells (having received only the carrier) as a function of the concentrations of $H_2O_2$, of ATA-Zn or of the comparative substances.

b) Assay 1: Determination of the Effective Doses of Ata-Zn and of its Toxicity

The ARPE-19 cells were treated with various concentrations of ATA-Zn ($10^{-3}$ to $10^{-9}$ M) dissolved in a carrier consisting of a serum-free culture medium containing 0.01% of DMSO (concentration known not to affect cell viability). The ATP production by the ARPE-19 cells thus treated was determined 24 hours after the addition of ATA-Zn. The ATP production by control cells treated only with the serum-free culture medium containing 0.01% of DMSO (carrier) was also determined.

Figure 4:
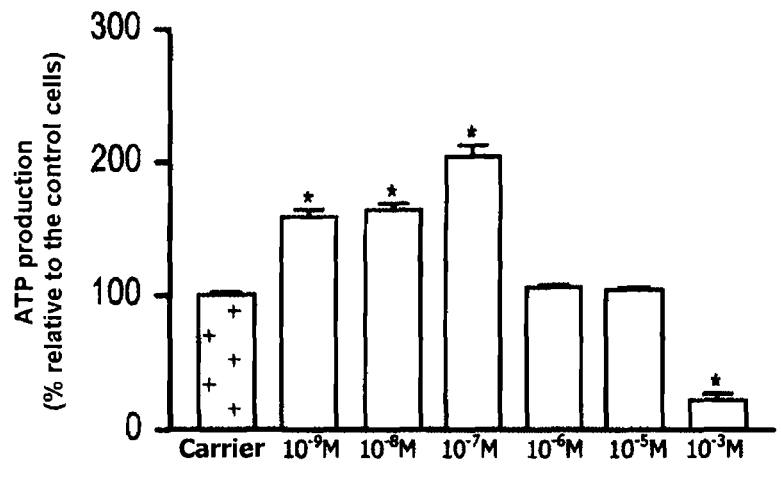
FIGS. 4-9 are graphs showing protective effects of ATA-ZN at various concentrations.

The results obtained, reported in FIG. 4, show that the low concentrations of ATA-Zn ($10^{-9}$ M, $10^{-8}$ M and $10^{-7}$ M) are capable of inducing an increase in cell viability, whereas higher concentrations ($10^{-3}$ M) are toxic for these cells.

c) Assay 2: Anti-Oxidative Stress Cytoprotective Effect

Figure 5:
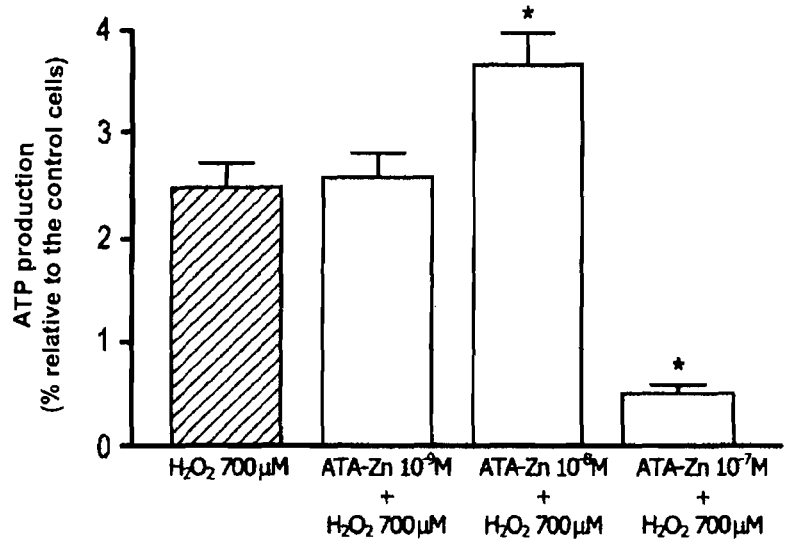
Figure 6:
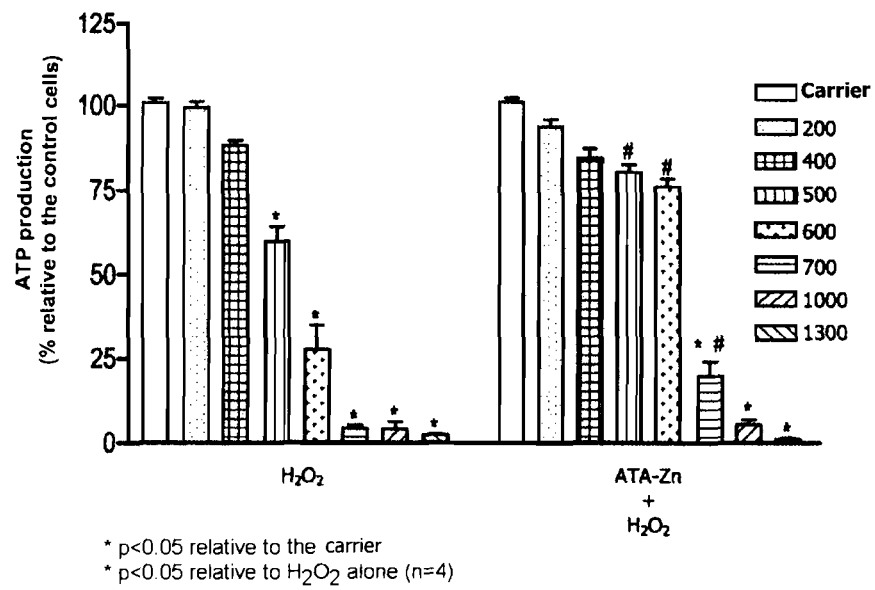

In this assay, the concentrations of ATA-Zn which induce a significant ATP production via the ARPE-19 cells were used, and then, after 1.5 hours, the cells were subjected to a treatment with $H_2O_2$ at the toxic dose of 700 µm. The results obtained, given in FIG. 5, show that ATA-Zn is capable of protecting the cells against oxidative stress, only at the concentration of $10^{-8}$ M, whereas, at the concentration of $10^{-9}$ M, ATA-Zn is not effective and at the concentration of $10^{-7}$ M, it even potentiates the toxic effect of $H_2O_2$.

d) Assay 3: Cytoprotective Effect of Ata-Zn on Cells Subjected to Oxidative Stress The ARPE-19 cells were exposed to various concentrations of $H_2O_2$ (expressed in µM) in the absence or presence of ATA-Zn at $10^{-8}$ M (treatment for one and a half hours before exposure to $H_2O_2$). The results reported in FIG. 6 show that ATA-Zn is capable of protecting the ARPE-19 cells against oxidative stress induced by various concentrations of $H_2O_2$. In fact, the toxic concentrations of $H_2O_2$ were not capable of significantly affecting the viability of the cells when said cells were pretreated with ATA-Zn.

Figure 7:
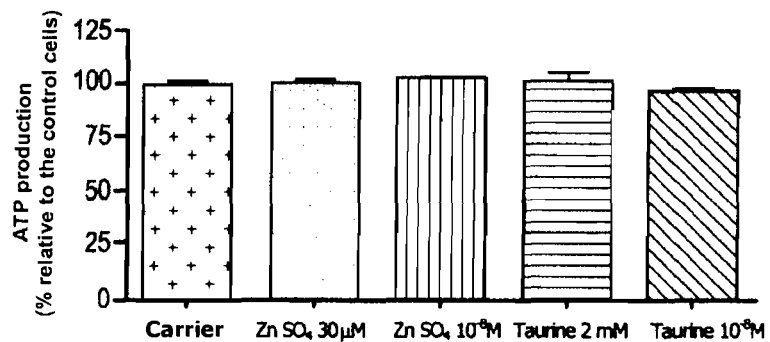
Figure 8:
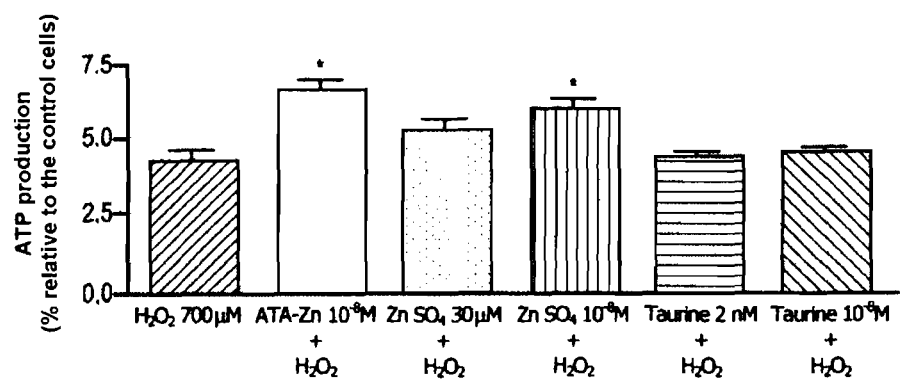
Figure 9:
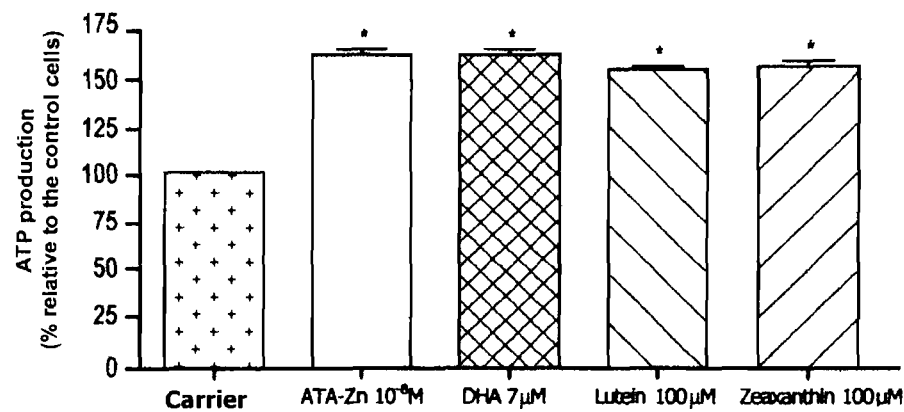

The above assays show that ATA-Zn can potentially play a therapeutic role in the treatment of the various pathological conditions of the retinal epithelium subjected to oxidative stress.

e) Comparative Assay No. 1: Determination of the Effective Doses of Taurine and of $ZnSo_4$ In this assay, the effect of taurine or of N-acetylated taurine and of zinc sulfate on ARPE-19 cell proliferation was compared. Taurine was used at two concentrations (2 mM and $10^{-8}$ M) and zinc sulfate was used at the following concentrations: 30 µM and $10^{-8}$ M. The results given in FIG. 7 show that neither zinc sulfate nor taurine at the various concentrations used were capable of inducing a significant proliferative effect on the ARPE-19 cells.

f) Comparative Assay No. 2: Determination of the Cytoprotective Effect in Oxidizing Medium To determine the antioxidant effect of zinc sulfate, of taurine or of N-acetylated taurine and of ATA-Zn, the ARPE-19 cells were pretreated with various concentrations of $ZnSO_4$, of taurine or of N-acetylated taurine and of ATA-Zn. The cells were then subjected, for 24 hours, to treatment with aqueous hydrogen peroxide solution at 700 µM. The results obtained, which are given in FIG. 8, confirm the ability of ATA-Zn to protect the ARPE-19 cells against oxidative stress. It will be noted that zinc sulfate at the concentration of $10^{-8}$ M induces a protective effect which is less than that of ATA-Zn. Taurine and zinc sulfate at the concentration of 30 µM were not capable of protecting the cells against the oxidative stress induced by $H_2O_2$.

g) Comparative Assay No. 3: Comparison with the Known Antioxidants DHA, Lutein and Zeaxanthin In this assay, the effect of ATA-Zn was compared with that obtained with DHA, lutein and zeaxanthin, which are commonly used in clinical and preclinical studies, in particular for their antioxidant properties and in the treatment of age-related macular degeneration. The results in FIG. 9 show that ATA-Zn has an effect comparable to the known antioxidants.

The invention claimed is:

1. A method for treatment of a lipofuscin accumulation-related disease and/or inhibiting lipofuscin accumulation in at least one organ tissue selected from the group consisting of retina, hippocampus and prostate, which comprises administering to a subject suffering from the disease an effective amount of zinc N-acetyltaurinate.

2. The method as claimed in claim 1, wherein the lipofuscin accumulation-related disease results from aging.

3. The method as claimed in claim 1, wherein the lipofuscin accumulation-related disease results from oxidative stress.

4. The method as claimed in claim 1, wherein the lipofuscin accumulation-related disease is at least one disease selected from the group consisting of age-related macular degeneration and diabetic retinopathy.

5. The method as claimed in claim 1, wherein the zinc N-acetyltaurinate is administered in a daily dose from 0.06 g to 10 g.

6. The method as claimed in claim 1, wherein the zinc N-acetyltaurinate is administered via an oral route or a parenteral route.

7. The method as claimed in claim 1, which wherein the method delays at least one disease selected from the group consisting of age-related macular degeneration and diabetic retinopathy.

* * * * *